United States Patent [19]

Lau et al.

[11] Patent Number: 5,096,833
[45] Date of Patent: Mar. 17, 1992

[54] METHOD AND DEVICE FOR DETERMINING PROTEIN USING CARRIER MATRIX COMPOSED OF URETHANE, WATER INSOUBLE INORGANIC COMPOUND AND INSOLUBLE ORGANIC COMPOUND AND METHOD OF MAKING THE DEVICE

[75] Inventors: Arthur L. Y. Lau, Granger; James H. Pendergrass, South Bend; Carrie A. Ritucci, Elkhart, all of Ind.

[73] Assignee: Miles Inc., Elkhart, Ind.

[21] Appl. No.: 529,643

[22] Filed: May 29, 1990

[51] Int. Cl.$^5$ .................. G01N 21/78; G01N 33/68
[52] U.S. Cl. .................. 436/86; 422/56; 422/57; 427/2; 427/407.1; 428/241; 428/243; 428/260; 428/160; 428/290; 428/423.1; 436/88; 436/169; 436/170; 435/805; 435/970; 521/159
[58] Field of Search .................. 521/159; 422/55–57; 435/805, 970; 436/86–88, 169, 170; 427/2, 408, 411, 407.1; 428/241, 243, 260, 270–275, 290, 160, 423.1

[56] References Cited

U.S. PATENT DOCUMENTS

| | | |
|---|---|---|
| 3,095,277 | 6/1963 | Free et al. . |
| 3,438,737 | 4/1969 | Atkinson et al. . |
| 3,485,587 | 12/1969 | Keston . |
| 4,166,093 | 8/1979 | Smith-Lewis et al. ........ 422/56 |
| 4,438,067 | 3/1984 | Siddiqi . |
| 4,466,931 | 8/1984 | Tanny ........................ 264/22 |
| 4,661,526 | 4/1987 | Ford ........................... 521/53 |

Primary Examiner—Robert J. Hill, Jr.
Attorney, Agent, or Firm—Roger N. Coe

[57] ABSTRACT

A test device and method of determining the presence and concentration of proteins in a test sample are disclosed. The test device includes a test pad comprising a new and improved carrier matrix incorporating an indicator reagent composition capable of interacting with proteins to produce a detectable or measurable response. The new and improved carrier matrix of the test pad comprises a film, membrane or layer of a polymerized urethane-based compound, a water insoluble inorganic compound and an insoluble organic compound. The carrier matrix provides improved color resolution and increased sensitivity to proteins in dry phase test strip assays, thereby achieving an accurate and trustworthy protein assay of a liquid test sample, such as urine, having a protein concentration as low as about 5 mg/dL. Also disclosed is a method of making the test device.

36 Claims, 3 Drawing Sheets

METHOD AND DEVICE FOR DETERMINING PROTEIN USING CARRIER MATRIX COMPOSED OF URETHANE, WATER INSOUBLE INORGANIC COMPOUND AND INSOLUBLE ORGANIC COMPOUND AND METHOD OF MAKING THE DEVICE

FIELD OF THE INVENTION

The present invention relates to an improved test device and method of assaying a test sample for the presence and concentration of proteins. More particularly, the present invention relates to a new and improved method and device for assaying a liquid, such as urine, for proteins by utilizing a test device having a test pad comprising an indicator reagent composition incorporated into a new and improved carrier matrix. The test pad undergoes a detectable or measurable response upon contact of the indicator reagent composition with a protein-containing liquid. The new and improved carrier matrix comprises a film, membrane or layer of a polymerized urethane-based compound that provides improved color resolution and increased protein sensitivity upon contact between the indicator reagent composition and the protein-containing test sample. Consequently, more accurate detection and measurement, either visually or by instrument, of the total protein content of a liquid test sample is achieved. In addition, the present invention relates to incorporating an indicator reagent composition into a new and improved carrier matrix to provide a test pad of a test device in an improved method to determine the protein concentration, and especially a low protein concentration, such as a protein concentration as low as about 5 mg/dL (milligrams per deciliter), in a test sample by a dry phase, test strip assay procedure.

BACKGROUND OF THE INVENTION AND PRIOR ART

Albumin is the most abundant plasma protein, generally constituting slightly over one-half of the total protein in mammalian plasma. In the human body, albumin has the important role of regulating the water balance between blood and tissues, and of functioning as a transport molecule for various compounds, such as bilirubin, fatty acids, cortisol, thyroxine and drugs such as sulfonamides and barbiturates, that are only slightly soluble in water. An albumin deficiency can restrict the transport of slightly water soluble materials throughout the body and a deficiency is signaled in an individual by an abnormal accumulation of serous fluid, or edema. Therefore, it is clinically important to determine whether an individual has a deficiency of serum albumin.

Likewise, it is clinically important to determine if an individual is excreting an excess amount of protein. A normal functioning kidney forms urine i essentially a two step process. Blood flows through the glomerulus, or glomerular region of the kidney. The capillary walls of the glomerulus are highly permeable to water and low molecular weight components of the blood plasma. Albumin and other high molecular weight proteins cannot pass through these capillary walls and are essentially filtered out of the urine so that the protein is available for use by the body. The liquid containing the low molecular weight components passes into the tubules, or tubular region, of the kidney where reabsorption of some urine components, such as low molecular weight proteins; secretion of other urine components; and concentration of the urine occurs. As a result, through the combined processes of the glomerulus and tubules, the concentration of proteins in urine should be minimal to absent. Therefore, abnormally high amounts of albumin or other proteins in urine must be detected and related to a physiological dysfunction.

The relatively high concentration of albumin in the urine of an individual usually is indicative of a diseased condition. For example, the average normal concentration of protein in urine varies from about 2 mg/dL to about 8 mg/dL, with approximately one-third of the total urinary protein being serum albumin. However, in a majority of diseased states, urinary protein levels increase appreciably, such that albumin accounts for from about 60 percent to about 90 percent of the excreted protein. The presence of an abnormal increased amount of protein in the urine, known as proteinuria, is one of the most significant indicators of renal disease, and may be indicative of various other non-renal related diseases.

Therefore, in order to determine if an individual either has an albumin deficiency or excretes an excess amount of protein, and in order to monitor the course of medical treatment to determine the effectiveness of the treatment, simple, accurate and inexpensive protein detection assays have been developed Furthermore, of the several different assay methods developed for the detection or measurement of protein in urine and serum, the methods based on dye binding techniques have proven especially useful because dye binding methods are readily automated and provide reproducible and accurate results.

In general, dye binding techniques utilize pH indicator dyes that are capable of interacting with a protein, such as albumin, and that are capable of changing color upon interaction with a protein absent any change in pH. When a pH indicator dye interacts with, or binds to, a protein, the apparent $pK_a$ (acid dissociation constant) of the indicator dye is altered and the dye undergoes a color transition, producing the so-called "protein-error" phenomenon. In methods utilizing the dye binding technique, an appropriate buffer maintains the pH indicator dye at a constant pH to prevent a color transition of the pH indicator dye due to a substantial shift in pH. Due to the "protein-error" phenomena, upon interaction with the protein, the pH indicator dye undergoes a color transition that is identical to the color change arising because of a change in the pH. Examples of pH indicator dyes used in the dry phase assay of proteins that are capable of interacting with or binding to proteins and exhibiting "protein-error" color transitions include tetrabromophenol blue and tetrachlorophenol-3,4,5,6-tetrabromosulfophthalein.

Although pH indicator dyes have been used extensively in protein assays, several disadvantages still exist in protein assay methods utilizing indicator dyes. For example, methods based upon pH indicator dyes either cannot detect or cannot quantitatively differentiate between protein concentrations below approximately 15 mg/dL. In addition, although several simple semiquantitative tests and several complex quantitative tests are available for the determination of the total protein content in a test sample, the majority of these assay methods, with the notable exception of the simple colorimetric reagent test strip, require the precipitation of protein to make quantitative protein determinations.

The colorimetric reagent test strip utilizes the previously discusses ability of proteins to interact with certain acid-base indicators and to alter the color of the indicator without any change in the pH. For example, when the indicator tetrabromophenol blue is buffered to maintain a constant pH of approximately 3, the indicator imparts a yellow color to solutions that do not contain protein. However, for solutions containing protein, the presence of protein causes the buffered dye to impart either a green color or a blue color to solution, depending upon the concentration of protein in the solution.

Some colorimetric test strips used in protein assays have a single test area consisting of a small square pad of a carrier matrix impregnated with a buffered pH indicator dye, such as tetrabromophenol blue. Other colorimetric test strips are multideterminant reagent strips that include one test area, or test pad, for protein assay as described above, and further include several additional test pads on the same strip to permit the simultaneous assay of other urinary constituents. For both types of colorimetric test strips, the assay for protein in urine is performed simply by dipping the colorimetric test strip into a well mixed, uncentrifuged urine sample, then comparing the resulting color of the test pad of the test strip to a standardized color chart provided on the colorimetric test strip bottle.

For test strips utilizing tetrabromophenol blue, buffered at pH 3, as the indicator dye, semiquantitative assays for protein can be performed and are reported as negative, trace, or one "plus" to four "plus". A negative reading, or yellow color, indicates that the urine contains no protein, as demonstrated by the lack of a color transition of the indicator dye. A trace reading may indicate from about 5 to 20 mg/dL of protein in the urine. The one "plus" to four "plus" readings, signified by color transitions of green through increasingly dark shades of blue, are approximately equivalent to urine protein concentrations of 30, 100, 300, and over 2000 mg/dL, respectively, and serve as reliable indicators of increasingly severe proteinuria.

In accordance with the above-described method, an individual can readily determine, visually, that the protein content of a urine sample is in the range of 0 mg/dL to about 30 mg/dL. However, the color differentiation afforded by the presently available commercial test strips is insufficient to allow an accurate determination of protein content in urine between 0 mg/dL and about 15 mg/dL. The inability to detect and differentiate between low protein concentrations is important clinically because a healthy individual usually has a urine protein level in the range of about 10 mg/dL to about 20 mg/dL. Therefore, it could be clinically important to know more precisely the urine protein content of an individual, rather than merely estimating the protein content at some value less than about 30 mg/dL.

Of course, the protein content of a urine sample can be determined more precisely by semiquantitative protein precipitation techniques or by quantitative 24 hour protein precipitation techniques. However, these tests are time consuming and relatively expensive. Furthermore, the precipitation tests must be run in a laboratory by trained personnel, and therefore are unavailable for the patient to perform at home to quickly determine urine protein content and to monitor the success or failure of a particular medical treatment.

Therefore, it would be extremely advantageous to have a simple, accurate and trustworthy method of assaying urine for protein content that allows visual differentiation of protein levels in the ranges of 0 mg/dL to about 5 mg/dL, about 5 mg/dL to about 10 mg/dL, and about 10 mg/dL to about 15 mg/dL, and upwards to between about 30 mg/dL to about 300 mg/dL. By providing such an accurate method of determining urine protein concentration in an easy to use form, like a dip-and-read test strip, the urine assay can be performed by laboratory personnel to afford immediate test results, such that a diagnosis can be made without having to wait up to one day for assay results and medical treatment can be commenced immediately. In addition, the test strip method can be performed by the patient at home to more precisely monitor low levels of protein in urine and/or the success of the medical treatment the patient is undergoing. Finally, the method and test device used in a protein assay should not adversely affect or interfere with other test pads that are present on a multi-determinant test strip.

As will be described more fully hereinafter, the method of the present invention allows the fast, accurate and trustworthy protein assay of urine by utilizing a test strip that includes a test pad comprising a new and improved carrier matrix incorporating an indicator reagent composition. The new and improved carrier matrix comprises a film, membrane or layer of a polymerized urethane-based compound that, surprisingly and unexpectedly, substantially improves the sensitivity and accuracy of protein assays by enhancing the color resolution and color differentiation of the assay. Accordingly, urine protein concentrations can be determined accurately at levels as low as about 5 mg/dL. Therefore, in general, the carrier matrix of the present invention provides an improved color resolution of the color transition resulting from contact of the protein-containing test sample with the indicator reagent composition. Consequently, assay sensitivity is improved, and the detection and measurement of protein content in liquids at levels as low as about 5 mg/dL is achieved.

Macroproteinuria or microproteinuria resulting either from abnormally high or abnormally low albumin levels depends upon the precise nature of the clinical and pathological disorder and upon the severity of the specific disease. Proteinuria can be intermittent or continuous, with transient, intermittent proteinuria usually being caused by physiologic or functional conditions rather than by renal disorders. Therefore, accurate assays of urine and other test samples for protein must be available for both laboratory and home use. The assays must permit the detection or measurement of proteins such that a correct diagnosis can be made and correct medical treatment implemented, monitored and maintained. In addition, it would be advantageous if the protein assay method, either for high concentrations of proteins or for low concentrations of proteins, is in a dip-and-read format for the easy and economical, qualitative or quantitative determination of protein in urine or other test samples.

Furthermore, any method of assaying for protein in urine or other test samples must yield accurate, trustworthy and reproducible results by utilizing a method that provides a detectable or measurable color transition as a result of an interaction between the indicator reagent composition and the protein, and not as a result of a competing chemical or physical interaction, such as a pH change or preferential interaction with a test sample component other than protein. Moreover, it would be advantageous if the protein assay method is suitable for use in dry reagent strips for the rapid, economical and accurate determination of protein in urine and other test samples. Additionally, the method and test pad, comprising the carrier matrix and the indicator reagent composition, utilized in the assay for protein should not adversely affect or interfere with the other test reagent pads that are present on multideterminant test strips.

Prior to the present invention, no known method of assaying urine or other test samples for proteins utilized a test device including a test pad comprising an indicator reagent composition homogeneously incorporated into a carrier matrix comprising a film, membrane or layer of a polymerized urethane-based compound. The new carrier matrix provides improved color resolution and increased assay sensitivity compared to present day carrier matrices, thereby achieving accurate and trustworthy protein assays for protein concentrations as low as about 5 mg/dL.

In addition, although a dry phase chemistry test strip utilizing a dye, such as tetrabromophenol blue or tetrachlorophenol-3,4,5,6-tetrabromosulfonephthalein, has been used extensively for several years, no dry phase test strip has utilized a test pad comprising a film, membrane or layer of a polymerized urethane-based compound. The carrier matrix improves color resolution and increases assay sensitivity, especially at lower protein concentration levels, such as protein levels of about 15 mg/dL and less. Furthermore, until the method of the present invention, dry phase test strip procedures were available principally to test for total protein concentration, i.e., for albumin, only down to levels as low as about 30 mg/dL. However, surprisingly and unexpectedly, because of the increased assay sensitivity afforded by the new and improved carrier matrix, the method of the present invention provides a dry phase test strip assay of urine and other test samples for protein down to levels as low as about 5 mg/dL.

The prior art contains numerous references on the wet phase and the dry phase chemistry utilized in the pH indicator dye method of assaying urine for proteins. For example, Keston U.S. Pat. No. 3,485,587 discloses the basic dye binding technique used to assay for proteins at a constant pH. Keston teaches utilizing a single indicator dye, maintained at a constant pH slightly below the $pK_a$ (acid dissociation constant) of the dye and impregnated into a dry test paper, like filter paper, to determine the presence or concentration of albumin by monitoring the color transition of the dye. Free, et al., in U.S. Pat. No. 3,095,277, also discloses a method of detecting the albumin content of liquid test samples by incorporating a suitable indicator composition into a bibulous carrier matrix, like untreated filter paper. Similarly, Atkinson et al. in U.S. Pat. No. 3,438,737 discloses a test device comprising a test composition impregnated into an untreated bibulous matrix, such as filter paper, wood strips, synthetic plastic fibrous materials, nonwoven fabrics and woven fabrics for detecting protein in fluids.

Japanese Patent No. 60-49256 is directed to a water phase protein assay utilizing an indicator composition including Coomassie Brilliant Blue dye, methylcellulose, and an acid having a $pK_a$ of from zero to four. The wet phase assay for proteins utilizing Coomassie Brilliant Blue dye also is described in the publication by M. M. Bradford, "A Rapid and Sensitive Method for the Quantitation of Microgram Quantities of Protein Utilizing the Principle of Protein Dye Binding", *Anal.Bio.* 72, 248–256 (1976). However, although this wet phase assay is sensitive to low protein concentrations, the wet phase assay also is impractical and cumbersome compared to a dry phase assay. For example, the Coomassie Brilliant Blue dye leads to excessive staining of glassware and other assay apparatus. In contrast, a dry phase test strip is discarded after use thereby avoiding costly and time-consuming manipulative steps, such as cleaning the stained glassware and other assay apparatus.

Smith-Lewis et al., in U.S. Pat. No. 4,166,093, disclosed a multi-layered dry phase test device including a layer comprising a polymer and, optionally, a finely-divided particulate material. This polymer-based layer is included in the test device to reflect, or absorb, detecting radiation and thereby facilitate detection of the analyte of interest. Wu et al. in U.S. Pat. No. 4,274,832 disclosed a similar radiation-blocking layer including either an opacifying agent, such as an inorganic metal salt, like titanium dioxide, or a non-fibrous, film-forming natural or synthetic polymer, like gelatin or a polyvinyl compound, or combinations thereof.

Siddiqi, in U.S. Pat. No. 4,438,067, disclosed a dry phase test device wherein distinct polymeric beads, incorporating the indicator reagent, were applied to a nonporous base, such as a plastic or a metal. The polymeric beads comprise a water-insoluble hydrophilic polymer, like cellulose and hydroxyacrylic polymers. The color transition resulting from contact of the test device with a test sample occurs within the beads. According to the method of Siddiqi, the indicator reagent is incorporated into the polymeric beads before the beads are applied to the support of the test device.

Tanny U.S. Pat. No. 4,466,931, described a method of manufacturing a permeable membrane by rapidly polymerizing a thin layer of a solution of a monomer or an oligomer to form an insoluble polymer. The solvent of the solution then is removed to provide a microporous membrane. Tanny disclosed a rapid polymerization of monomers or oligomers by ultraviolet or electron beam radiation to form a microporous membrane. Ford, in U.S. Pat. No. 4,661,526, disclosed a method of preparing a crosslinked, porous polymeric membrane formed from polyamides or polyamide/polyimide copolymers.

However, none of the above-cited references teaches or suggests either alone or in combination, that a carrier matrix, comprising a film, membrane or layer of a polymerized urethane-based compound, can be used in a diagnostic device to achieve a more accurate determination of the amount of an analyte, like protein, and especially low amounts of an analyte, like about 4 mg/dL, in a test sample. In contrast to the prior art, and in contrast to the presently available commercial test strips, the method of the present invention provides increased accuracy and increased sensitivity in the detection and measurement of proteins in a liquid test sample, such as a biological fluid, like urine. Surprisingly and unexpectedly, by utilizing a carrier matrix of the present invention, protein levels of about 30 mg/dL and below, down to about 5 mg/dL, can be determined accurately. Hence, in accordance with the method of the present invention, new and unexpected results are achieved in the dry phase reagent strip assay of urine and other test samples for proteins by utilizing a test pad including an indicator reagent composition incorporated into a carrier matrix comprising a film, membrane or layer of a polymerized urethane-based compound.

SUMMARY OF THE INVENTION

In brief, the present invention is directed to a new and improved test device, method of manufacturing the test device, and method of determining the presence or concentration of a component in a test sample. The device includes a test pad comprising an improved carrier matrix capable of incorporating an indicator reagent composition that interacts with a test sample component to produce a detectable response. The improved carrier matrix of the test pad comprises a film, membrane or layer of a polymerized urethane-based compound that improves the resolution and differentiation of the color transition resulting from contact of the test device with the test sample. For home use, the indicator reagent composition produces a visually detectable response. For laboratory use, the indicator reagent composition produces a response that is detectable visually or by instrument.

The new and improved carrier matrix of the device of the device of the present invention comprises a film, membrane or layer of a polymerized urethane-based compound An indicator reagent composition then is homogeneously incorporated into the carrier matrix, and the carrier matrix holds the indicator reagent composition homogeneously throughout the carrier matrix in a known concentration while maintaining carrier matrix penetrability by the test sample and by the test sample component to be assayed. Surprisingly and unexpectedly, it has been found that the method and test device of the present invention provides a more sensitive, accurate and reliable protein determination, whereby protein concentrations as low as about 5 mg/dL can be determined.

More particularly, the present invention is directed to a method of assaying urine or other test samples for proteins by utilizing a test device including a test pad comprising an indicator reagent composition and a new and improved carrier matrix. It has been demonstrated that incorporating an indicator reagent composition into a carrier matrix of the present invention, comprising a film, membrane or layer of a polymerized urethane-based compound, affords improved color resolution and increased sensitivity to proteins, and especially at low protein concentration ranges. In accordance with an important feature of the present invention, the qualitative or the quantitative determination of protein levels between 0 mg/dL and about 2000 mg/dL, and especially between 0 mg/dL and about 30 mg/dL, in urine and other test samples is accomplished. By utilizing the carrier matrix of the present invention in clinical test methods, the qualitative or quantitative concentration of protein, such as albumin, in urine or other test samples is determined more accurately because the film, membrane or layer of a polymerized urethane-based compound provides an improved color resolution of the color transition resulting from the interaction between the indicator reagent composition and the protein. Consequently, the sensitivity of the dry phase assay method to low concentrations of protein is increased.

Therefore, it is an object of the present invention to provide a new and improved test device and method for determining the relative concentration of a chemical compound in a liquid.

Another object of the present invention is to provide a simple, trustworthy, accurate and reproducible method of assaying urine or other liquid test samples for proteins.

Another object of the present invention is to provide a new and improved protein interactive test device for interaction with protein in a test fluid to produce a visible change, such as a change in color, of the test device, indicative of the protein concentration in the test fluid.

Another object of the present invention to provide a method of assaying urine or other liquid test samples for albumin.

Another object of the present invention is to provide a method of assaying urine or other liquid test samples that provides improved visual color resolution and increased sensitivity to low protein concentrations.

Yet another object of the present invention is to provide a method of assaying urine or other liquid test samples that is sensitive to protein concentrations as low as about 5 mg/dL and that quantitatively discriminates between protein levels of from 0 mg/dL to about 2000 mg/dL, and especially from 0 mg/dL to about 30 mg/dL.

Another object of the present invention is to provide a method of assaying urine or other liquid test samples that utilize a test device including a test pad comprising a carrier matrix comprising a film, membrane or layer of a polymerized urethane-based compound.

Another object of the present invention is to provide a method of assaying urine or other test liquids by utilizing an indicator reagent composition that, when incorporated into a carrier matrix comprising a film, membrane or layer of a polymerized urethane-based compound, can interact with proteins and undergo a detectable or measurable color transition to establish the presence or to measure the concentration of low levels of protein in the test sample.

Another object of the present invention is to provide a test device including a test pad comprising an indicator reagent composition incorporated into a new and improved carrier matrix including a protein-permeable film, membrane or layer of a polymerized urethane-based compound, that can interact with proteins and undergo a visually or instrumentally differentiable color transition to allow the quantitative determination of the concentration of protein in the urine or other liquid samples at levels between 0 mg/dL and about 2000 mg/dL, and especially between 0 mg/dL and about 30 mg/dL.

Another object of the present invention is to provide a method of manufacturing a detection device for proteins comprising a test pad including a carrier matrix comprising a film, membrane or layer of a polymerized urethane-based compound.

Another object of the present invention is to provide a new and improved test device and a method of manufacturing a test device including a test pad comprising a carrier matrix having incorporated therein, after or during manufacture thereof, an indicator reagent composition capable of interacting with a chemical compound in a test sample, wherein the carrier matrix, comprising a film, membrane or layer of a polymerized urethane-based compound, improves the resolution of the color transition resulting from contact of the test device with the test sample.

Another object of the present invention is to provide a new and improved method of manufacturing a test device used to detect the presence of a chemical compound in a liquid, wherein the chemical compound is capable of permeating a carrier matrix comprising a film, membrane or layer of a polymerized urethane-based compound and is capable of interacting with an indicator reagent composition that is incorporated into the carrier matrix.

A still further object of the present invention is to provide a new and improved dry phase test pad that incorporates an indicator reagent composition into a carrier matrix comprising a protein-permeable film, membrane or layer of a polymerized urethane-based compound, that achieves new and unexpected precision in protein response, and that does not interfere with assays performed by adjacent test pads on a multi-determinant test strip.

Another object of the present invention is to provide a new and improved test device for the quantitative analysis of proteins.

BRIEF DESCRIPTION OF THE DRAWINGS

The above and other object and advantages and novel features of the present invention will become apparent from the following detailed description of the preferred embodiments of the invention illustrated in the accompanying figures demonstrating the enhanced color resolution of the color transition in the test strips and the increased sensitivity of the test strips to proteins, thereby permitting more accurate quantitative analyte determinations.

DETAILED DESCRIPTION OF THE INVENTION

Figure 1:
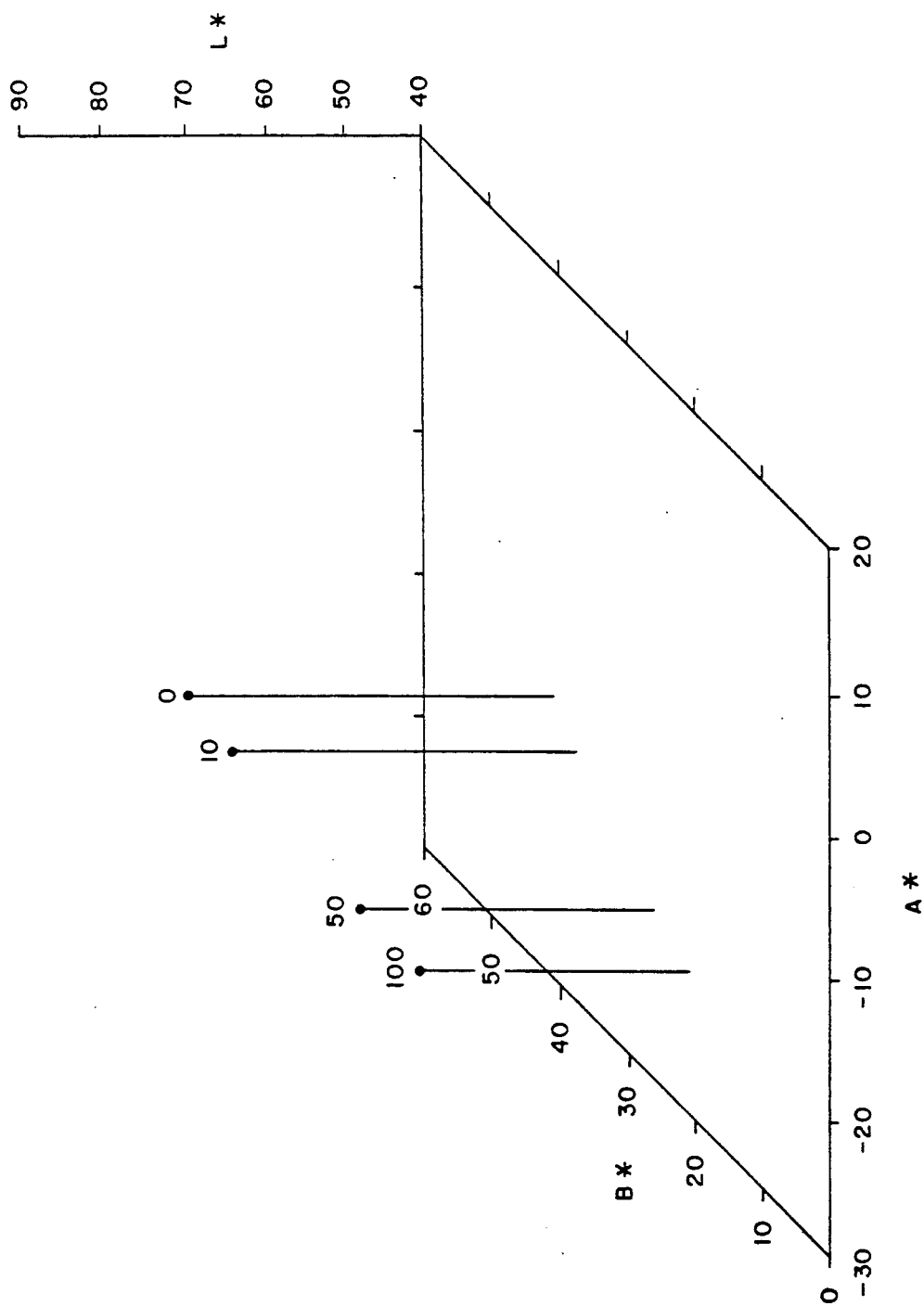
FIG. 1 is a color space plot showing the assay of liquid samples containing 0, 10, 50 and 100 mg/dL of albumin respectively using a dry phase test strip including a carrier matrix of untreated filter paper, and incorporating the indicator dye tetrabromophenol blue (TBPB)

In accordance with the method of the present invention, the qualitative or quantitative assay for proteins, including albumin, in urine and other liquid test samples is accomplished by utilizing a test device including a test pad comprising a carrier matrix incorporating an indicator reagent composition. The carrier matrix of the present invention comprises a film, membrane or layer of a polymerized urethane-based compound that improves the resolution of the color transition resulting from contact of the test device with the test sample, and therefore increases the sensitivity of the assay.

By using a test device that includes a test pad comprising the new and improved carrier matrix, visual and instrumental color resolution of an assay is improved over assays employing a test pad comprising an untreated fibrous, bibulous substrate as the carrier matrix and over assays employing a test pad comprising a treated fibrous, bibulous substrate. Consequently, the sensitivity of the assay to low protein concentrations is increased by utilizing the carrier matrix of the present invention in a test device. The improved color resolution, and the increased sensitivity to low protein levels, afforded by the carrier matrix of the present invention is especially useful in urine assays.

Present-day commercial assays are incapable of differentiating between protein levels ranging from 0 mg/dL to about 30 mg/dL, and especially from 0 mg/dL to about 15 mg/dL. Differentiating between low protein concentration levels is clinically important in the art because a range of from about 10 mg/dL to about 20 mg/dL is used as the normal urine protein level for a healthy individual. Therefore urine protein levels from 0 mg/dL to about 10 mg/dL, i.e., microalbuminuria, may indicate a potential protein deficiency that can cause physiological imbalances. Furthermore, urine protein levels greater than about 20 mg/dL may indicate an excessive excretion of proteins that can signify a diseased state. It should be noted that in regard to urine protein concentrations in the relatively high range, such as form about 100 mg/dL to about 2000 mg/dL, the method of the present invention still affords improved color resolution and increased sensitivity to urine protein concentration, however such clinical benefits are less critical in this relatively high concentration range since such high protein levels are definitely indicative of an abnormal physiological state that must be investigated further.

Furthermore, it will become apparent that in addition to assaying urine, the method and device of the present invention also can be used to determine the presence or quantitative concentration of albumin in blood plasma and serums: and more generally, the albumin content of many other albumin-containing fluids as well. In accordance with another important feature of the present invention, the method and device of the present invention is employed in dry phase, test strip assays to determine the presence or concentration of proteins in urine or other liquid test samples.

Surprisingly and unexpectedly, it has been found that a test pad comprising a suitable indicator reagent composition incorporated into a carrier matrix of the present invention has demonstrated improved color resolution and increased sensitivity to proteins, and especially to low protein concentrations, when used in a dye-binding technique to determine the presence or concentration of proteins in a test sample. The dye-binding technique using an indicator reagent composition incorporated into the carrier matrix of the present invention provides a more accurate, trustworthy and clinically significant quantitative assay for protein. Presently, dry phase test strip assays utilize either untreated bibulous substrates, such as filter paper, or treated bibulous substrates as the carrier matrix of a test pad used to determine the presence or concentration of protein in a test sample.

The indicator reagent compositions used in present day assay methods for protein interact with proteins and undergo a color transition due to the protein-error phenomena when maintained at the proper, constant pH. The protein-error phenomena is fully described in Free et al. U.S. Pat. No. 3,095,277; Atkinson et al. U.S. Pat. No. 3,438,737; and Keston U.S. Pat. No. 3,485,587, wherein the various dyes, the correct pH ranges, the buffers and the untreated carrier matrices, such as bibulous substrates, like filter paper, required to observe the protein-error phenomena are disclosed. The three above-identified patents basically describe the present day, dry phase test strips employed to assay for total protein content in urine. These total protein test strips generally include an indicator reagent composition comprising an indicator dye that normally undergoes a color transition at a strongly acidic pH of 5 or below and a buffer to maintain the pH of the indicator dye slightly below the pH of color transition for the dye. A sufficient buffering of the indicator dye essentially assures that the dye changes color due to an interaction with protein rather than due to a pH change occurring upon contact with the test sample. The present day total protein test strips further include a carrier matrix, usually untreated filter paper, for incorporation of the indicator reagent composition.

In accordance with an important feature of the present invention, it has been demonstrated that a new and improved carrier matrix, comprising a film, membrane or layer of polymerized urethane-based compound, provides a more accurate and trustworthy assay for total protein content in liquid samples. Furthermore, a method of fast, accurate, reproducible and trustworthy assays, performable at home or in the laboratory, to yield essentially immediate assay results for albumin is achieved.

Accordingly, an indicator reagent composition, including a suitable indicator dye, is incorporated into the carrier matrix of the present invention. A suitable dye is capable of interacting with proteins, and is capable of undergoing a sufficient color transition due to the protein-error phenomena upon interaction with a protein to give a detectable or measurable response. However, in accordance with the present invention, it has been found that incorporating a suitable indicator reagent composition into a carrier matrix comprising a film, membrane or layer of a polymerized urethane-based compound substantially improves the color resolution and differentiation, both visually and instrumentally, of the color transition occurring upon interaction of the indicator dye with proteins. Therefore, the sensitivity of the protein assay, especially at relatively low protein concentrations, is increased because of the carrier matrix of the present invention.

The method of the present invention utilizes the "protein-error" phenomena previously discussed. However, the incorporation of a suitable indicator reagent composition into a carrier matrix of the present invention improves the color resolution and differentiation of the color transition occurring because of the dye-protein interaction. As previously described, when a pH indicator dye interacts with a protein, the apparent $pK_a$ of the dye is altered and a color transition occurs producing the so-called "protein-error" phenomena. However, by employing the carrier matrix of the present invention, a more spectacular color development is achieved, therefore improving color resolution and color differentiation upon interaction between the indicator dye and proteins. Accordingly, assay sensitivity is increased.

In general, any pH indicator dye can be utilized in the method of the present invention, provided that the dye is capable of interacting with proteins and undergoing a detectable and measurable color transition in response to the protein interaction. Such indicator dyes as described above are well-known and are utilized in indicator reagent compositions in methods to determine the presence or the concentration of protein in urine or other liquid test samples. In addition to the indicator dyes, the indicator reagent composition also may require a sufficient amount of a proper buffer, such that the indicator dye will not change color as a result of a pH shift, but will change color upon contact and interaction with proteins to accurately establish the presence or the concentration of protein in the test sample. Further, it has been demonstrated that any of various known types of buffers can be used in the indicator reagent composition. In addition, it has been found that for optimum results, the pH of the indicator reagent composition generally should be maintained at a pH value only slightly below the pH range wherein the indicator dye of the indicator reagent composition undergoes a color transition. A method of determining a suitable buffered pH value for the particular indicator dye of the indicator reagent composition and of determining the particular buffer than can be used in the indicator reagent composition is found in Keston, U.S. Pat. No. 3,485,587.

Upon contact with the urine or other test sample, a color transition of the indicator reagent composition demonstrates the presence of protein. Furthermore, the intensity and degree of the color transition can be used to determine the concentration of protein in the test sample by comparing or correlating the color intensity produced by the test sample to color intensities produced by solutions having a known concentration of protein. In accordance with an important feature of the present invention, it has been demonstrated that the intensity and degree of color transition of the indicator reagent composition are surprisingly and unexpectedly increased when the indicator reagent composition is incorporated into a carrier matrix comprising a film, membrane or layer of a polymerized urethane-based compound. Consequently, the resulting color transition is sufficiently resolved and differentiated such that the amount of protein in the test sample can be measured and determined accurately without the use of color-measuring instruments, such as spectrophotometers or colorimeters. However, if desired, such color-measuring instruments can be used to measure the difference in color degree and intensity between the test sample and a solution of known albumin concentration.

Accordingly, an assay for protein that utilizes a test pad comprising an indicator reagent composition incorporated into the new and improved carrier matrix of the present invention improves the accuracy and reliability of the assay and also increases physician confidence in the assay. Additionally, because of the number of urine assays for protein being performed at home by the untrained patient, as opposed to trained physicians or technicians in the laboratory, it is imperative to provide accurate and reliable assay methods for protein content in the urine. Similarly, if the assay is performed on a multideterminant test strip, the carrier matrix of the present invention precludes the protein assay from interfering with assays for other urinary constituents performed by adjacent test pads, thereby further increasing physician or patient confidence in the assays.

The dry phase, test strip assay for protein that utilizes a test pad comprising an indicator reagent composition incorporated into the new and improved carrier matrix of the present invention is performed in accordance with methods well know in the art. In general, the assay for protein is performed by contacting the urine or other test sample with an analyte detection device that includes a test pad comprising an indicator reagent composition incorporated into the carrier matrix of the present invention. The analyte detection device can be dipped into the test sample, or the test sample can be applied to the analyte detection device dropwise. The resulting change in color of the analyte detection device demonstrates the presence of protein; and, if so designed, the resulting color transition can be compared to a standardized color chart to provide a quantitative measurement of the concentration of protein in the urine or test sample.

Typically, the prior art describes the analyte detection device as a test strip designed either as a single test pad test strip (to assay only for a single analyte) or as a multiple test pad test strip (to assay for several analytes simultaneously). For either type of test strip, the test strip includes a support strip, or handle, normally constructed from a hydrophobic plastic, secured to at least one test pad, comprising a bibulous or nonbibulous substrate and incorporating the indicator reagent composition. In general, the bibulous or nonbibulous substrate is an absorbent material that allows the test sample to move, in response to capillary forces, through the substrate to contact the indicator reagent composition and produce a detectable and measurable color transition.

The test pads of the prior art could be any substance capable of incorporating the chemical reagents required to perform the assay of interest, as long as the substrate, either bibulous or nonbibulous in nature, is substantially inert with respect to the chemical reagents, and is porous and/or absorbent relative to the liquid test sample. However, in accordance with an important feature of the present invention, the present test pad comprises a carrier matrix comprising a film, membrane or strip of a polymerized urethane-based compound. The carrier matrix of the present invention is insoluble in water and other physiological fluids and maintains its structural integrity when exposed to water and other physiological fluids. Hydrophobic and non-absorptive substances are not suitable for use as the polymerized urethane-based compound included in the carrier matrix of the present invention. The carrier matrix can be of different chemical compositions or a mixture of chemical compositions. The carrier matrix also can vary in regards to smoothness and roughness combined with hardness and softness. However, in every instance, the carrier matrix comprises a hydrophilic or absorptive material. In contrast, the handle of the test strip usually is formed from hydrophobic, non-absorptive materials such as polyethylene erephthalate, polycarbonate or polystyrene.

To achieve the full advantage of the present invention, the indicator reagent composition is incorporated into a carrier matrix comprising a film, membrane or layer of a polymerized urethane-based compound having a suitable pore shape and sufficient pore size distribution such that the film, layer or membrane can be uniformly permeated by proteins. The film, membrane or layer of polymerized urethane-based compound usually is manufactured before the indicator reagent composition is incorporated into the carrier matrix. The test pad, comprising the carrier matrix of the present invention incorporating the indicator reagent composition, then is utilized in a dry phase test strip for the assay of protein in a test sample. Therefore, in general, the method of the present invention provides an economical, accurate and reliable assay for the total concentration of proteins in a test sample. In addition, the method of the present invention can be performed at home or in the laboratory and allows the detection, differentiation and measurement of low protein concentrations, like down to about 5 mg/dL, in the test sample, therefore making the assay more useful clinically.

In accordance with the preferred embodiment of the present invention, the carrier matrix of the dry phase, test strip for protein first is prepared. The carrier matrix can be prepared directly on the hydrophobic handle; or the carrier matrix can be prepared on another suitable substrate, then secured to the hydrophobic handle by double-sided adhesive tape. The carrier matrix is manufactured from a composition containing a urethane compound. As will be described more fully hereinafter, the urethane-containing composition includes either a polymerizable urethane compound or a polymerized urethane compound, or a combination thereof. If a polymerizable urethane compound is utilized to manufacture the carrier matrix, the polymerizable urethane compound is polymerized by a suitable method, then cured, to provide the new and improved carrier matrix of the present invention comprising a film, membrane or layer of polymerized urethane-based compound. Alternatively, if the carrier matrix is manufactured from a composition including a polymerized urethane compound, the polymerization step can be omitted, and, after curing, the new and improved carrier matrix of the present invention is provided. To achieve the full advantage of the present invention, the carrier matrix is manufactured from a urethane compound that has been partially or completely polymerized.

A suitable indicator reagent composition then is incorporated into the carrier matrix by immersing the carrier matrix into a solution of the indicator reagent composition, or by spraying or spreading a solution of the indicator reagent composition onto the carrier matrix to form the test pad of the test device. The solvent of the indicator reagent composition is removed by oven drying in an air oven maintained at about 50° C. for about 20 to 30 minutes. Alternatively, the indicator reagent composition can be included in the composition containing a urethane compound, and therefore incorporated into the carrier matrix as the carrier matrix is being manufactured, such that after curing a test pad of the test device is manufactured. The test pad, comprising the carrier matrix incorporating the indicator reagent composition, then, if not formed directly on the hydrophobic handle, is cut to an appropriate size, such as a test pad having dimensions from about 0.25cm by about 0.5cm to about 0.5cm by about 1.0cm. The test pad comprising the carrier matrix incorporating the indicator reagent composition then is secured to an opaque or transparent hydrophobic plastic handle with double-sided adhesive tape.

Regardless of whether the test pad is formed directly on the hydrophobic handle or whether the test pad is adhesively secured to the hydrophobic handle, the resulting test device, or dry phase test strip, then is dipped into a fresh, uncentrifuged urine sample for a sufficient time to saturate the test pad with the sample. After waiting a predetermined time, such as from about 30 seconds to about 2 minutes, the test strip is examined, either visually or by instrument, for a response. The color transition, if any, of the test pad reveals the presence and/or concentration of protein the urine sample. Analogous to the prior art, it is well within the experimental techniques of those skilled in the art of preparing test devices to determine the proper balance between size of carrier matrix, the strength of indicator reagent composition solution, the amount of test sample, and the method of introducing the test sample to the test strip, such as by pipetting rather than dipping, in order to design a quantitative assay for protein utilizing the method and composition the present invention.

In many cases simple visual observation of the test strip provides the desired information. If more accurate information is required, a color chart bearing color spots corresponding to various known protein concentrations can be prepared for the particular indicator reagent composition used in the test strip. The color of the test strip resulting from contact with the urine sample then can be compared to the color spots on the chart to determine the protein concentration of the test sample.

If a still more accurate analyte determination is required, a spectrophotometer or colorimeter can be used to more precisely determine the degree of color transition. In addition, the dry phase, reagent strip assay can be made quantitative by employing spectrophotometric or colorimetric techniques, as opposed to visual techniques, in order to measure the degree of color transition more precisely and more reliably, and therefore more accurately measure the concentration of protein in the test sample, especially at low protein concentrations, such as below about 30 mg/dL.

As will be demonstrated more fully hereinafter, the carrier matrix of the present invention improves the detection, the differentiation between, and the measurement of low concentrations of proteins in a test sample. Accordingly, the improved sensitivity of the carrier matrix of the present invention provides a method of accurately assaying a test sample having a protein concentration as low as about 5 mg/dL. In contrast, present day dry phase test strips can detect and measure protein concentrations only as low as about 15 mg/dL. Therefore, according to present day methods, the detection of low protein concentrations below about 15 mg/dL requires a heat and precipitation technique that is expensive and time consuming. Consequently, until the method of the present invention, no dry phase, test strip technique was available to accurately detect and measure low concentrations of proteins, such as below about 15 mg/dL, in a test sample, like urine.

As previously discussed, a dry phase test strip used for the assay of proteins in test samples generally includes a test pad having a carrier matrix that is amenable to incorporation of a suitable indicator reagent composition; that permits the urine or other test sample to permeate the carrier matrix rapidly enough to obtain protein assays relatively quickly; and that does not contaminate the urine or other test sample either by test sample extraction of components comprising the carrier matrix or by appreciably altering the urine or test sample in a way to make the subsequent assays inconclusive, inaccurate or doubtful. Such a carrier matrix, upon incorporation of a suitable indicator reagent composition, provides a test pad that allows the detection or accurate measurement of protein in liquid test samples.

However, the prior art test pads, comprising an indicator reagent composition incorporated into a carrier matrix comprising either an untreated bibulous (i.e., filter paper) or nonbibulous (i.e., polymeric) substrate, or a carrier matrix comprising a treated bibulous substrate, did not allow the accurate protein determination of test samples containing from 0 mg/dL to about 30 mg/dL of protein. Surprisingly and unexpectedly, unlike the untreated bibulous and nonbibulous substrates of the prior art and unlike the treated bibulous substrates the new and improved carrier matrix used in the method and test device of the present invention allows the measurement and detection of low levels of albumin in a test sample, such as from 0 mg/dL to about 30 g/dL.

For the test strip of the present invention, designed to assay for the total protein content of a test sample, the carrier matrix is a film, membrane, or layer of a polymerized urethane-based compound that allows the test sample to permeate and saturate the test pad of the test strip and to contact the indicator reagent composition. To achieve the full advantage of the present invention, the carrier matrix of a test pad used to assay for the total protein content of a test sample comprises a protein-permeable film, membrane or layer formed from a urethane-containing composition including a urethane polymer, a urethane prepolymer or a combination thereof. The untreated filter paper and related bibulous substrates of the prior art possessed sufficient porosity for proteins, such as albumin, to penetrate the bibulous substrate, and contact and interact with the incorporated indicator reagent composition to produce a color transition. However, a carrier matrix of the present invention possesses sufficient porosity and also unexpectedly improves color resolution and differentiation of the color transition to provide a more sensitive assay for proteins. Therefore, a protein assay of increased accuracy and reliability is provided.

In accordance with an important feature of the present invention, the carrier matrix can be prepared by various methods. For example, the carrier matrix can be manufactured from a composition including a polymerized urethane compound dispersed in a suitable liquid vehicle. The composition is applied to a substrate as a wet film, then cured and dried to provide a carrier matrix comprising a film, membrane or layer of a polymerized urethane-based compound of a the desired configuration, such as pore size distribution and pore shape. Alternatively, the carrier matrix can be manufactured from a composition including a polymerizable urethane compound dispersed in a suitable liquid vehicle. Accordingly, this polymerizable composition is applied to a substrate as a wet film, then the polymerizable urethane compound first is polymerized. Next, the polymerized urethane-based compound is cured and dried to provide a carrier matrix of the present invention having the desired configuration. Consequently, then by incorporating a suitable indicator reagent composition into a carrier matrix of the present invention, a test pad for a test device and method of detecting or differentiating between different levels of albumin, and especially between low levels of albumin, such as from 0 mg/dL to about 30 mg/dL, in a test sample is provided. Therefore, a test pad comprising a carrier matrix of the present invention demonstrates improved color resolution, improved color differentiation and increased sensitivity when employed in a dry phase, test strip assay for proteins, such as albumin.

As will be demonstrated in the embodiments of the present invention described hereinafter, if the carrier matrix is manufactured from a composition including a polymerizable urethane compound dispersed in a suitable liquid vehicle, the polymerizable urethane compound first is polymerized to yield a polymerized urethane compound. Then the polymerized urethane compound, dispersed in a suitable liquid vehicle, is cured either by a water bath, by a sonicator bath containing water or by heating the polymerized urethane compound to produce the polymerized urethane-based compound. If a polymerized urethane compound is used to manufacture the carrier matrix, the polymerization step is omitted, but the curing step is included in order to provide a carrier matrix having a polymerized urethane-based compound of the preferred configuration for assaying for proteins. Furthermore, in each case, the carrier matrix comprising a protein-permeable film, membrane or layer of a polymerized urethane-based compound has a suitable indicator reagent composition incorporated therein before the carrier matrix is used in a test device to detect proteins.

It has been found that in order to provide the new and improved carrier matrix of the present invention, a polymerizable urethane compound or a polymerized urethane compound, such as a urethane prepolymer, first is dispersed or dissolved in a suitable liquid vehicle. Similarly, a mixture of a polymerizable urethane compound and a polymerized urethane compound, dispersed or dissolved in a suitable liquid vehicle, can be used in the manufacture of the carrier matrix of the present invention. Then the resulting dispersion or solution, after application onto a suitable substrate as a wet film, is formed into the carrier matrix by removing the liquid vehicle from the dispersion for solution during curing of the urethane-containing composition. Removing the liquid vehicle during curing allows the urethane compound to dry and coagulate as a continuous film, membrane or layer having the preferred pore size and pore shape to assay for proteins.

The urethane compound dispersed or dissolved in a suitable liquid vehicle can be polymerizable or polymerized, and includes oligomers, prepolymers, incompletely cured polymers and mixtures thereof. In addition, depending upon the solubility and chemical properties of the indicator reagent composition, the urethane-containing composition can be mixed with the indicator reagent composition prior to curing, and the test pad then is manufactured by curing the urethane-containing composition to form the carrier matrix. The test pad comprising the carrier matrix incorporating the indicator reagent composition is cut into strips, then into pads, and secured to a plastic handle.

It has been found that the urethane-containing composition, including a polymerizable or polymerized urethane compound like an oligomer, prepolymer, incompletely cured polymer or mixtures thereof, dispersed in a continuous liquid vehicle forms a permeable film, membrane or layer upon removal of the continuous liquid vehicle phase during the curing process. Accordingly, a carrier matrix having a suitable pore shape, pore size and pore size distribution to assay for proteins is provided. The urethane compound, after dissolving or dispersing in a continuous liquid vehicle phase can be cured in any know manner. Further, the solution or dispersion of the urethane compound can include a suitable curing catalyst or can be heat cured provided that the solution or dispersion of the urethane compound is applied as a layer in the form of an incompletely cured solution or dispersion. Generally, urethane compounds useful in accordance with the present invention are those that can be dissolved or dispersed in a liquid vehicle, such as an organic solvent, like an aprotic solvent or an alcohol, and that can be cured to yield an essentially colorless, protein-permeable and continuous film, membrane or layer upon curing.

In accordance with one embodiment of the present invention, the urethane compound is a polymerizable urethane prepolymer, and particularly a urethane prepolymer comprising essentially repeating urethane units wherein the prepolymer chain is terminated at each end with isocyanate functionalities. It has been found that the urethane compound can be either neutral or cationic in electronic character, or a combination of a neutral urethane compound and a cationic urethane compound can be used. To achieve the full advantage of the present invention, it has been found that the polymerizable urethane compound, or a polymerized urethane compound, is neutral in electronic character. Example of a suitable commercial urethane prepolymers include DESMODERM KBH GRANULATE and DESMODERM KPK DISPERSION, available commercially from BAYER AG.

The expression "urethane prepolymer" is understood to describe an essentially linear polymer or repeating urethane units. The urethane prepolymer has at least two isocyanate functionalities per molecule, and the polyurethane prepolymer should have a weight average molecular weight ($M_w$) of at least about 50,000. Urethane prepolymers with weight average molecular weights below about 50,000, for example down to about 30,000, also are useful as long as the prepolymers are soluble or dispersible in a liquid vehicle and can be cured to form a continuous film, membrane or layer. The maximum $M_w$ is one wherein the urethane prepolymer can be solubilized or otherwise dispersed in a continuous liquid vehicle phase, such as a suitable organic solvent like and aprotic solvent or an alcohol. For the incompletely-cured dispersed urethane prepolymer, weight average molecular weights of up to about 500,000 are expected to be practical for the present invention. Upon curing, there is no upper limit to the molecular weight of the film, membrane or layer. It has been found that, to achieve the full advantage of the present invention, the $M_w$ for the polymerizable urethane prepolymer is within the $M_w$ range of about 70,000 to about 80,000.

In accordance with another embodiment of the present invention, the urethane compound is a cationic or, preferably, a neutral polymerized urethane compound. The urethane compound also can be a combination of a cationic polymerized urethane polymer and a neutral polymerized urethane polymer. The polymerized urethane polymer has a weight average molecular weight ($M_w$) in the same general range as the urethane prepolymers and is soluble or dispersible in the continuous liquid vehicle. The carrier matrix of the present invention is manufactured from a composition including a polymerized urethane compound by contacting a wet film of the solution or dispersion of the polymerized urethane compound with water to cause a phase separation and agglomeration and entanglement of the polymer chains. Subsequent heating of the water-cured film removes the remaining solvent and the water to provide a dry permeable film. Alternatively, the solution or dispersion of the polymerized urethane polymer can be cured by omitting the water step and simply by heating the wet film.

The polymerizable or polymerized urethane compound, such as a urethane prepolymer, useful in the method of the present invention can include other monomeric units that are incorporated into the polymerizable urethane compound by copolymerizing an isocyanate containing monomer, hydroxyl containing monomer and a suitable third monomeric unit into the urethane prepolymer. In addition, although the polymerizable or polymerized urethane compound useful in the method of the present invention is preferentially neutral in nature, anionic or cationic polymerizable of polymerized urethane compounds also are envisioned as being useful.

More particularly, a prepolymer found useful in the method of the present invention, DESMODERM KBH, is a neutral thermoplastic granular polymerized urethane material, obtained by reacting 75 parts of a polyester of adipic acid, including 70 mol % ethylene glycol and 30 mol % 1,4-butanediol ($M_w=2,000$); 25 parts of a polyester of adipic acid and 1,4-butanediol ($M_w=2,250$); 25 parts 1,4-butanediol; and 85 parts diphenylmethanediisocyanate. Cationic urethanes in general are formed by a reaction of a polyisocyanate, a polyol and a hydroxyl-containing tertiary amine, wherein the amine portion of the polyurethane is subsequently neutralized with an organic acid, followed by dispersion of the neutralized polymerized urethane in water. Accordingly, DESMODERM KPK is a cationic, emulsifier-free polymerized urethane dispersion of a reaction product of 200 parts of a polyester of adipic acid, phthalic acid and ethylene glycol ($M_w=1,700$); 50 parts toluenediisocyanate; 20 parts N-methyldiethanolamine; and 6 parts p-xylylene dichloride.

In accordance with the present invention, the particular urethane compound utilized in the present invention, after mixing with the other components of the urethane-containing composition, such as the continuous liquid vehicle, is cured to produce a polymeric film, membrane or layer that has a physical structure permeable to proteins. Generally, the urethane compound is present in the urethane-containing composition in a range of from about 0.1% by weight to about 10% by weight, and preferably from about 1% by weight to about 5% by weight, based upon the total weight of the urethane-containing composition. Furthermore, it should be understood that the urethane-containing composition can contain either a neutral urethane compound, a cationic urethane compound or a mixture of a neutral urethane compound and a cationic urethane compound.

As will be discussed more fully hereinafter, the carrier matrix of the present invention affects the degree of color resolution and the sensitivity of the protein assay. The percentage of urethane compound used in the urethane-containing composition, and the nature of the urethane compound, either neutral, cationic, or a neutral/cationic mixture, affects the degree of color resolution, the stability of color production, and the speed of color production. Therefore, in accordance with the method of the present invention, analyte test devices including a urethane-based carrier matrix of the present invention can be designed for improved color resolution, increased color stability, or faster color production as required.

In addition to the polymerizable or polymerized urethane compound, the urethane-containing composition used in the manufacture of the carrier matrix includes a dispersed inorganic phase, wherein the inorganic phase includes a water-insoluble inorganic compound. The urethane-containing composition includes from about 1% by weight to about 10% by weight, and preferably from about 2% by weight to about 5% by weight, based on the total weight of the urethane-containing composition, of a water-insoluble inorganic compound, such as barium sulfate, as a filler. The exact identity of the inorganic compound used as a filler is unimportant as long as the filler is essentially white in color, and does not interfere with the color detection and measurement resulting from interaction between the indicator dye and the protein; and as long as the inorganic filler is essentially water-insoluble, such that dissolved anions and cations are not available to interfere chemically or physically with the protein assay. Therefore, insoluble inorganic compounds that can be used in accordance with the method of the present invention include calcium sulfate, titanium dioxide, alumina, zinc oxide, magnesium oxide, calcium oxide, silicon dioxide, talc, magnesium aluminum oxide, magnesium titanium oxide, barium oxide, barium sulfate, strontium sulfate and other similar, essentially white, water-insoluble inorganic compounds, especially oxides; or mixtures thereof.

The insoluble inorganic compound is incorporated into the urethane-containing composition as a powder to help assure uniform dispersion of the insoluble inorganic compound throughout the urethane-containing composition. In addition, by utilizing an insoluble inorganic compound in powder form, the insoluble inorganic compound is maintained uniformly dispersed throughout the urethane-containing composition during the curing process. The uniform dispersion of the insoluble inorganic compound provides a polymerized urethane-based film, layer or membrane having the insoluble inorganic compound uniformly dispersed throughout the film, layer or membrane.

The urethane-containing composition also includes from about 10% to about 40%, and preferably from about 20% to about 35%, by weight of the total composition of an insoluble organic filler, such as microcrystalline cellulose. Similar to the inorganic filler, the insoluble organic filler is added to the composition as a powder to ensure a homogeneous dispersion of the insoluble organic filler throughout the urethane-containing composition and throughout the polymerized urethane-based film. In addition, the insoluble organic filler preferably is essentially white in color and is sufficiently water-insoluble to preclude interference with the protein assay. In accordance with the present invention, the organic filler is included in the urethane-containing composition, in addition to the inorganic filler, to improve film coherence, film thickness and film wettability. Accordingly, other suitable organic fillers include microcrystalline nitrocellulose and other microcrystalline cellulosic materials.

The urethane-containing composition also can include surfactants to help wet the insoluble inorganic compound and the insoluble organic filler, and therefore assist in homogeneously dispersing the inorganic compound and the organic filler throughout the urethane-containing composition. The surfactants can be present from 0% by weight up to approximately 5% by weight, based on the total weight of the urethane-containing composition. The surfactant also may act to help stabilize the color resulting from contact between protein and the indicator reagent composition.

The surfactants found useful in the method of the present invention are not necessarily limited to a particular type, and include, generally, anionic sufactants, like ammonium, alkylammonium, potassium and/or sodium dodecylbenzene sulfonates, alkyl sulfates, alkyl ether sulfates, dioctyl sulfosuccinate, alpha olefin sulfonates, and alkyl sarcosinates; or mixtures thereof. Similarly, nonionic surfactants, such as the polyethylene glycols, polypropylene glycols, ethoxylated alcohols, nonoxynols and octoxynols, as are well known in the art, can be used in the urethane-containing composition. It should be understood that the above listed anionic and nonionic surfactants are presented only as nonlimiting examples of surfactants that can be included in the urethane-containing composition. In general, a surfactant included in the urethane-containing composition is not limited to a particular type or class of surfactant as long as the surfactant does not adversely affect the carrier matrix in regard to providing a sensitive and accurate assay for proteins.

In addition, other surface active agents, such as silicon-containing materials, like a polydimethylsiloxane fluid, can be incorporated into the urethane-containing composition in weight percentages of up to 2% based upon the total weight of the urethane-containing composition. These silicon-containing materials possess a low surface tension, and therefore further assist in wetting the insoluble inorganic compound and the organic filler. The silicon-containing materials also reduce the surface tension of the urethane-containing composition to provide a leveling effect, thereby producing a smooth and "polished" polymerized urethane-based film, membrane or layer of uniform thickness.

The urethane-containing composition also optionally includes from 0% to about 6% by weight of the composition of a water-soluble cellulose derivative, like hydroxypropylcellulose, available under the trade name KLUCEL from Hercules, Inc., Wilmington, Del. The water-soluble cellulose derivative acts to increase the pore size of the film. Accordingly, other suitable water-soluble cellulose derivatives include sodium carboxymethylcellulose, ethoxylated cellulose, hydroxyethylcellulose, hydroxybutylcellulose and hydroxylpropylcellulose; or combinations thereof. In addition to, or in replacement of, the water-soluble cellulose derivatives, water-dispersible compounds such as xanthan gum, guar gum, alginates, silicone gums, carboxymethyl guar, hydroxypropyl guar, ghatti gum, karaya gum, carrageenans, tragacanth gum, arabic gum, agar gum or locust bean gum optionally can be included in the urethane-containing composition.

As discussed previously, the urethane-containing composition also includes a liquid vehicle, such as an organic solvent, capable of solubilizing or dispersing the urethane compound and any surfactants or silicon-containing materials that may be present. The liquid vehicle also must be capable of dispersing the insoluble inorganic compound and the insoluble organic filler. The liquid vehicle should be relatively inert such that it will not react with the urethane compound, and the liquid vehicle should evaporate at relatively low temperatures to provide a dry carrier matrix film, membrane or layer after curing of the urethane-containing composition. It has been demonstrated that organic aprotic solvents, such as dimethylformamide, N-methyl pyrrolidone, and dimethyl sulfoxide, or mixtures thereof, provide the required solvency to dissolve and disperse the components of the urethane-containing composition; provide the required inertness to preclude interaction between the liquid vehicle and the urethane compound: and possess the required vapor pressure to yield a solvent-free polymerized urethane-based film, membrane or layer.

Similarly, the lower alcohols, such as an alcohol including from one to about four carbon atoms, like methyl alcohol, ethyl alcohol, n-propyl alcohol, isopropyl alcohol, n-butyl alcohol, sec-butyl alcohol, isobutyl alcohol and tert-butyl alcohol, have been found to possess the necessary solvency, inertness and vapor pressure to yield a solvent-free polymerized urethane-based film. Such lower alcohols can be used alone, in combination with another lower alcohol or in combination with the aprotic solvents described above. The liquid vehicle, substantially removed during curing, is included in the urethane-containing composition in an amount of at least about 40%, and up to about 88.9% by weight, based on the total weight of the urethane-containing composition.

It also has been found that utilizing a liquid vehicle comprising an aprotic solvent and an alcohol reduces the curing time needed to remove the liquid vehicle from the urethane-containing composition. For example, a 10 minute curing time is needed to sufficiently remove a liquid vehicle consisting exclusively of N-methyl pyrrolidone; a 2 minute curing time is needed to sufficiently remove a liquid vehicle consisting exclusively of dimethylformamide; whereas only about 30 seconds is needed to sufficiently remove a liquid vehicle comprising a 60:40 ratio by weight of dimethylformamide to methyl alcohol. Therefore, a suitable choice of liquid vehicle significantly reduces the time needed to complete the curing step.

In accordance with an important feature of the present invention, urethane-containing compositions were prepared from the formulations presented in Examples 1 and 2. As will be discussed more fully hereinafter, the urethane-containing compositions of Examples 1 and 2, then were applied as a wet film to a hydrophobic plastic handle, and cured to form a carrier matrix of the present invention. After curing, a suitable indicator reagent composition was incorporated into the carrier matrix to form a test pad used to assay standardized albumin solutions by the normal dip-and-read test strip procedure.

| Urethane-Containing Composition | |
|---|---|
| EXAMPLE 1 | |
| DESMODERM KBH (Neutral Urethane) | 2.9% |
| Microcrystalline Cellulose | 24.3% |
| Barium Sulfate | 2.8% |
| Dimethylformamide | 70.0% |
| TOTAL | 100.0% |
| EXAMPLE 2 | |
| DESMODERM KBH (Neutral Urethane) | 2.6% |
| Hydroxypropylcellulose | 0.6% |
| Microcrystalline cellulose | 24.0% |
| Barium Sulfate | 2.8% |
| Dimethylformamide | 70.0% |
| TOTAL | 100.0% |

In preparing each of the urethane-containing compositions of Examples 1 and 2, the urethane compound DESMODERM KBH first was premixed with a minor amount of the dimethylformamide to provide a homogeneous mixture. Similarly, if present, the hydroxypropylcellulose also first is premixed with a minor amount of the dimethylformamide to provide a second homogeneous mixture. Then, the components of Examples 1 and 2 were combined and thoroughly mixed using a high speed mixer until a homogeneous urethane-containing composition resulted.

To prepare a carrier matrix of the present invention, either the composition of Example 1 or the composition of Example 2 is applied, or coated, onto the transparent, impermeable plastic support, like polyethylene terephthalate (PET), as a wet film. The thickness of the wet film coating of the composition is controlled by using a doctor blade adjusted to a wet thickness of from about 150u (microns) to about 750u. After coating the plastic support with the urethane-containing composition, the coated plastic support is immersed into a circulating water bath maintained at a constant temperature of about 25° C. to about 43° C. for about 5 minutes to about 30 minutes. Then the urethane-containing composition can be cured completely by immersing the partially-cured coated plastic support in a room temperature water bath for a time period ranging from about 30 minutes to about 16 hours. After complete curing, the coated plastic support is air-dried or oven-dried to provide a carrier matrix of the invention, comprising a film, membrane or layer of a polymerized urethane-based compound.

Although the above-described process is the preferred curing process, alternatively, a urethane-containing composition coated onto the plastic support can be cured either by placing the coated plastic support into a sonicator bath containing water, then sonicating for about 30 seconds, 1 minute or 2 minutes, followed by oven drying at about 80° C. for about 20 minutes; or by eliminating the water curing step and curing the urethane-containing composition coated onto the plastic support by oven drying at about 80° C. for about 20 minutes. It should be noted that the water curing step can be eliminated entirely. However, the performance of a test pad comprising a carrier matrix of the present invention that has been cured in water is superior to a test pad comprising a carrier matrix of the present invention that has not been cured in water. The superior results demonstrated by the water-cured carrier matrix theoretically may be attributed to a more complete liquid vehicle removal during water curing and to a more preferred polyurethane pore shape and pore size distribution that results from the water curing.

Normally, after curing the urethane-containing composition to form a polymerized urethane-based compound, the resulting carrier matrix of the present invention has an indicator reagent composition incorporated therein to form a test pad. However, if the reagents comprising the indicator reagent composition are soluble in the liquid vehicle used in the manufacture of the urethane-containing composition, like dimethylformamide or an alcohol, and if the reagents comprising the indicator reagent composition are insoluble in water, then the indicator reagent composition can be incorporated into the urethane-containing composition and coated onto the hydrophobic plastic with the urethane-containing composition prior to curing.

To show the new and unexpected results arising from using a test device including a test pad comprising the carrier matrix of the present invention incorporating a suitable indicator reagent composition, color space plots were made for protein assays to detect and measure the amount of protein in a test sample. The assays utilized dry phase test strips having different test pads, such as a test pad comprising an indicator reagent composition incorporated into an untreated filter paper bibulous matrix; a test pad comprising an indicator reagent composition incorporated into a carrier matrix comprising a fibrous, bibulous substrate homogeneously impregnated with a polymerized urethane-based compound; and a test pad comprising an indicator reagent composition incorporated into a carrier matrix of the present invention.

Figure 2:
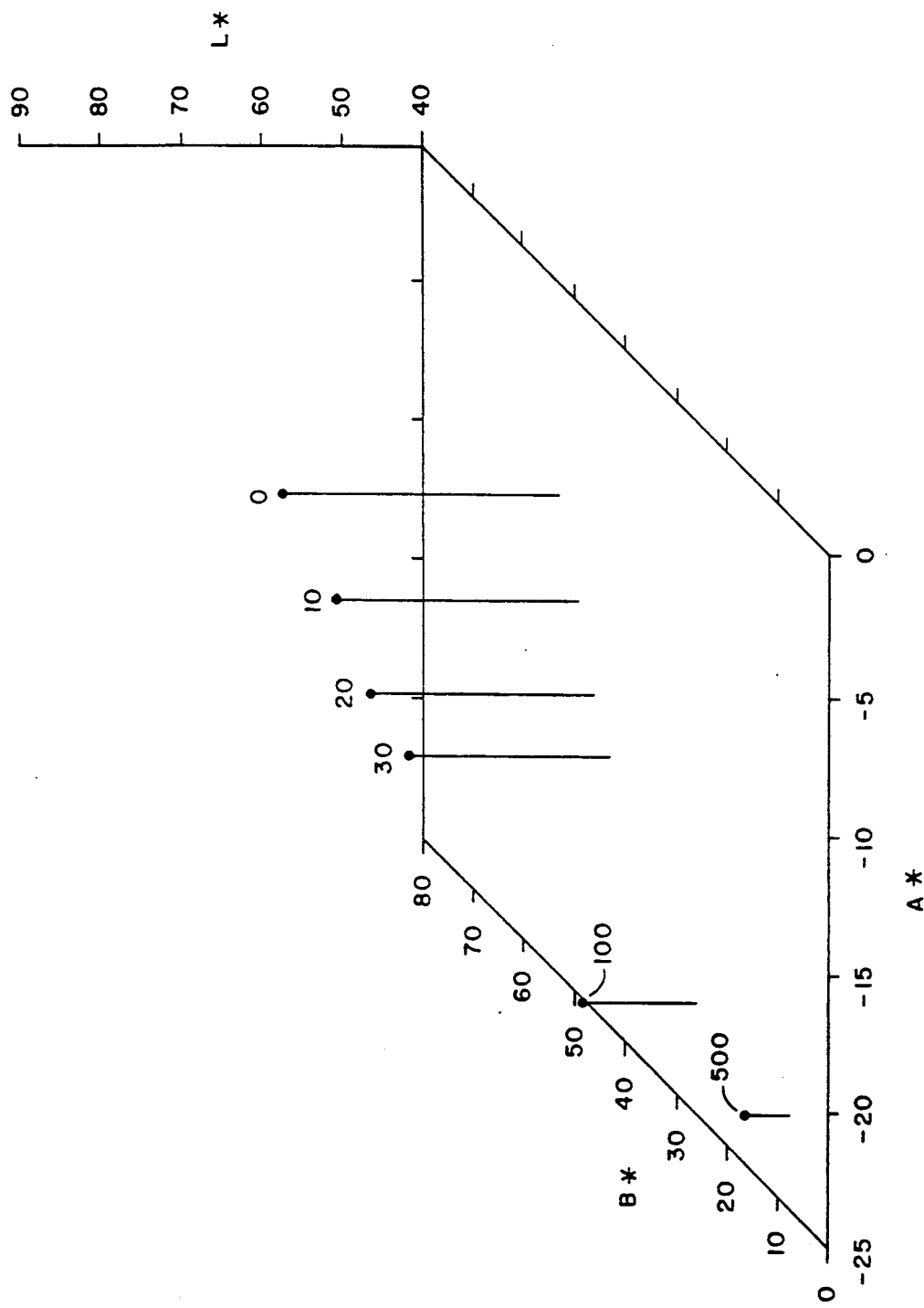
FIG. 2 is a color space plot showing the assay of liquid samples containing 0, 10, 20, 30, 100 and 500 mg/dL of albumin respectively using a dry phase test strip including a carrier matrix comprising a filter paper substrate homogeneously impregnated with a polymerized urethane-based compound, and incorporating the indicator dye tetrabromophenol blue (TBPB)
Figure 3:
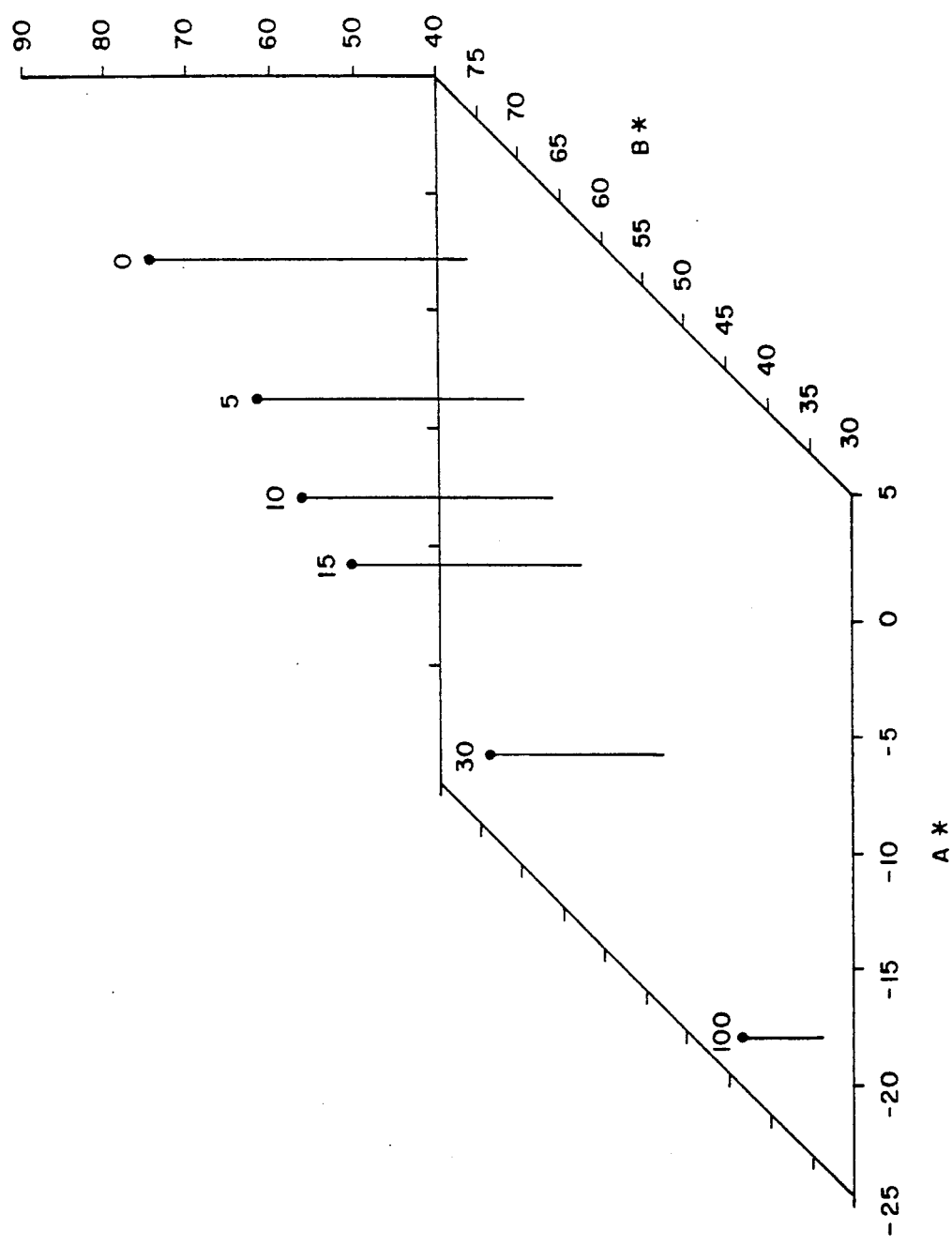
FIG. 3 is a color space plot showing the assay of liquid samples containing 0, 5, 10, 15, 30, and 100 mg/dL of albumin respectively using a dry phase test strip including a carrier matrix comprising a film of a polymerized urethane-based compound, and incorporating tetrabromophenol blue (TBPB) as the indicator dye.

FIGS. 1 through 3 are color space plots obtained from contacting standardized albumin solutions with various dry phase test strips including a test pad comprising an indicator reagent composition incorporated into either a carrier matrix comprising untreated filter paper (FIG. 1); or a carrier matrix comprising a filter paper substrate homogeneously impregnated with a polymerized urethane-based compound (FIG. 2); or a carrier matrix of the present invention comprising a protein-permeable film, membrane or layer of a polymerized urethane-based compound (FIG. 3).

For example, FIG. 1 is the color space plot resulting from contacting a dry phase test strip with a a standardized solution containing no albumin (0), 10 mg/dL albumin (10), 50 mg/dL albumin (50) or 100 mg/dL albumin (100). The test strip includes a test pad comprising an indicator reagent composition, including tetrabromophenol blue (TBPB) buffered with a citrate buffer, incorporated into an untreated filter paper carrier matrix. FIG. 2 is a color space plot resulting from protein assays using dry phase test strips including a test pad comprising the TBPB indicator reagent composition incorporated into a carrier matrix including WHATMAN CCP500 filter paper homogeneously impregnated with a polymerized urethane-based compound. WHATMAN CCP500 filter paper is available commercially from Whatman Ltd., Maidenhead, Kent, U.K. The filter paper was impregnated with a 2% by weight solution of DESMODERM KBH in dimethylformamide, followed by a curing step, then a drying step. These dry phase test strips contacted standardized albumin-containing solutions including no albumin (0), 10 mg/dL albumin (10), 20 mg/dL albumin (20), 30 mg/dL albumin (30), 100 mg/dL albumin (100) and 500 mg/dL albumin (500). FIG. 3 is a color space plot resulting from protein assays using dry phase test strips including a test pad comprising the TBPB indicator reagent composition incorporated into a carrier matrix of the present invention. The dry phase test strips including a carrier matrix of the present invention, manufactured from the urethane-containing composition of Example 1, contacted standardized albumin-containing solutions including no albumin (0), 15 mg/dL albumin (15), 30 mg/dL albumin (30) and 100 mg/dL albumin (100).

As illustrated in FIGS. 1 through 3, a color space plot includes three axes, the $L^*$, $A^*$ and $B^*$ axes. The values of $L^*$ plotted on the vertical axis are a measure of the intensity of color, whereby a large $L^*$ value denotes a light color and $L^*=0$ denotes a completely black color. The horizontal $A^*$ axis is a measure of the color transition from green to red, whereby the more positive the $A^*$ value, the more red the color, and analogously, the more negative the $A^*$ value, the more green the color. Similarly, the third axis, $B^*$, is a measure of the color transition from blue to yellow, whereby the greater the value of $B^*$, the more yellow the color, and analogously the smaller the value of $B^*$, the more blue the color.

The color space difference ($\Delta E$) is calculated from the following equation:

$$\Delta E = \sqrt{(L_1^* - L_2^*)^2 + (A_1^* - A_2^*)^2 = (B_1^* - B_2^*)^2} \qquad \text{Eq. 1}$$

wherein:

$L_1^*$, $A_1^*$, and $B_1^*$ are the color space values determined for a first standardized protein solution;

$L_2^*$, $A_2^*$, and $B_2^*$ are the color space values determined for a second standardized protein solution having a different protein concentration from the first standardized protein solution; and ΔE is the color space difference between the color space plots of the first and second standardized protein solutions.

The color space difference (ΔE) is the straight line distance between two points in a three-dimensional color space plot. Theoretically, a color space difference of one color block is the smallest color difference the human eye can distinguish. However, because of the inherent differences between the visual capabilities of individuals, a color space difference (ΔE) of about 5 color blocks is required in order to practically and confidently distinguish between colors.

The L*, A* and B* values plotted on the color space plots of FIGS. 1 through 3 are calculated from the percent reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values X, Y and Z, and L*, A* and B* are calculated from the X, Y and Z tristimulus values using the following equations:

$$L^* = 116 \times [(Y/Y_o)^{1/3} - 16)] \quad \text{(Eq. 2)}$$

$$A^* = 500 \times [(X/X_o)^{1/3} - (Y/Y_o)^{1/3}] \quad \text{(Eq. 3)}$$

$$B^* = 200 \times [(Y/Y_o)^{1/3} - (Z/Z_o)^{1/3}] \quad \text{(Eq. 4)}$$

wherein $X_o$, $Y_o$ and $Z_o$ are the tristimulus values for perfect white (i.e. reflectance=100% at all wavelengths), and X, Y and Z are the tristimulus values calculated as described above from the sixteen wavelengths between 400 nm and 700 nm.

From the color space plots of FIGS. 1 through 3, the color space differences (ΔE) were calculated, and summarized in TABLE I. In interpreting TABLE I, the term, ΔE(Alb 10-0) is the color space difference between protein assays for protein solutions containing 10 mg/dL of albumin and 0 mg/dL of albumin. Similarly, the term ΔE(Alb50-0) is the color space difference between protein assays for protein solutions containing 50 mg/dL of albumin and 0 mg/dL of albumin. The terms ΔE(Alb100-0 and ΔE(Alb500-0) are analogously defined.

TABLE I

| FIG. NO. | CARRIER MATRIX | ΔE (Alb5-0) | ΔE (Alb10-0) | ΔE (Alb15-0) | ΔE (Alb20-0) | ΔE (Alb30-0) | ΔE (Alb50-0) | ΔE (Alb100-0) | ΔE (Alb500-0) |
|---|---|---|---|---|---|---|---|---|---|
| | COLOR SPACE DIFFERENCES (ΔE) FOR PROTEIN ASSAYS USING A TBPB INDICATOR REAGENT COMPOSITION INCORPORATED INTO VARIOUS CARRIER MATRICES | | | | | | | | |
| 1 | Untreated Filter Paper | — | 4.8 | — | 9.9 | 12.1 | 19.2 | 25.5 | 36.1 |
| 2 | Filter Paper Impregnated with Polymerized Urethane-Based Compound | — | 6.6 | — | 12.3 | 16.8 | — | 37.2 | 55.6 |
| 3 | Polymerized Urethane-Based Compound | 9.6 | 14.4 | 18.9 | — | 31.6 | — | 54.3 | — |

0 = Albumin 0 mg/dL
Alb5 = Albumin 5 mg/dL
Alb10 = Albumin 10 mg/dL
Alb15 = Albumin 15 mg/dL
Alb20 = Albumin 20 mg/dL
Alb30 = Albumin 30 mg/dL
Alb50 = Albumin 50 mg/dL
Alb100 = Albumin 100 mg/dL
Alb500 = Albumin 500 mg/dL As illustrated in the color space plot of FIG. 1 and in TABLE I, protein assays were conducted on standardized albumin solutions with a dry phase test strip including a test pad having the indicator, buffered tetrabromophenol blue (TBPB), incorporated into an untreated filter paper matrix. From FIG. 1 and TABLE I, it is seen that the color space difference between a solution containing no albumin is 4.8 color blocks. Because the human eye normally can differentiate only between colors having a color space difference of approximately 5 color blocks, this assay would be inconclusive as to whether the sample contained any albumin because the color differentiation between the test strip contacting the 0 mg/dL albumin solution and the test strip contacting the 10 mg/dL albumin. TABLE I and FIG. 1 further show that the human eye can detect color differences resulting from the presence of 20 mg/dL, 30 mg/dL, 50 mg/dL and 100 mg/dL of albumin because the color space differences are 9.9, 12.1, 19.2 and 25.5 color blocks, respectively.

By homogeneously impregnating a filter paper substrate with a polymerized urethane-based compound, the color resolution and differentiation of the color transition improves to permit and assayer to visually differentiate between samples containing 0 mg/dL of albumin and 10 mg/dL albumin. From FIG. 2 and TABLE I, a color space difference (ΔE) between a solution containing 10 mg/dL of albumin and a solution containing no albumin is 6.6 color blocks when using a test device including a test pad incorporating an indicator reagent composition into a carrier matrix comprising filter paper impregnated with a polymerized urethane-based compound. Such a color space difference is sufficient to be discernible by the human eye; shows a substantial improvement over the color space difference afforded by the untreated filter paper matrix of FIG. 1; and allows the detection and measurement of protein levels in a test sample down to about 10 mg/dL. Similarly, TABLE I and FIG. 2 show the enhanced color differentiation for the 20 mg/dL, 30 mg/dL, 100 mg/dL and 500 mg/dL albumin solutions compared to the solution containing no albumin.

However, from FIG. 3 and TABLE I, surprisingly and unexpectedly, by using a test device including a carrier matrix of the present invention, the color resolution and differentiation of the color transition is improved further to permit an assayer to visually differentiate between samples containing 0 mg/dL of albumin and 5 mg/dL albumin. A color space difference of 9.6 between a solution containing 5 mg/dL and a solution containing no albumin is observed when using a test device including a test pad incorporating an indicator reagent composition into a film, membrane or layer of a polymerized urethane-based compound. This color difference is readily discernible by the human eye and demonstrates a substantial improvement over the carrier matrices of the test devices used to generate the color space plots of FIG. 1 and FIG. 2. Similar results are observed when using a test device including a carrier matrix manufactured from the urethane-containing composition of Example 2.

It is observed that when a test pad of the present invention is used, the color space difference (9.6) between a solution containing 5 mg/dL and a solution containing no albumin is substantially greater than the color space difference (6.6) between a solution containing 10 mg/dL and a solution containing no albumin that is assayed by a test pad including filter paper impregnated with a polymerized urethane-based compound. Accordingly, a test device of the present invention can be used to accurately assay a test sample for protein at concentrations as low as about 5 mg/dL. In addition, the color space difference observed for assays utilizing a test device of the present invention were greater across the entire concentration range of proteins. Therefore, color resolution and differentiation are improved, and assay results are more accurate.

Overall, FIGS. 1 through 3 and TABLE I show that an indicator reagent composition incorporated into a carrier matrix comprising a film, membrane or layer of a polymerized urethane-based compound improves the color resolution and assay sensitivity in an assay for the total protein content of a liquid test sample, especially at low protein levels about 30 mg/dL and less. In contrast to the prior art, the method and device of the present invention allow visual differentiation of color transition resulting from contact between the indicator reagent-containing carrier matrix and a test sample containing protein at a level of about 5 mg/dL, thereby providing more accurate and trustworthy assays.

To further demonstrate the benefits and advantages provided by the carrier matrix of the present invention, a present day, commercial test strip used to assay for protein was compared to carrier matrices of the present invention manufactured from the compositions of Examples 1 and 2. The commercial test strip was an ALBUSTIX test strip, available from Miles Inc., Elkhart, IN. The ALBUSTIX test strip includes a test pad comprising the buffered tetrabromophenol (TBPB) indicator reagent composition incorporated into a carrier matrix. To manufacture the carrier matrices of the present invention, a composition of Example 1, or a composition of Example 2, was applied to a plastic handle with a doctor blade to provide a wet film having a wet thickness of about 750 μ (microns). After applying a wet film of a urethane-containing composition of Example 1 or Example 2 to a plastic handle, the wet film was cured and dried in accordance with the previously described water-curing method. After curing and drying, the carrier matrix was impregnated with the TBPB indicator reagent composition, and the resulting test pad was used to assay standardized solutions for protein content.

The assay for albumin was performed by dipping the test strip into the protein-containing solution for a time sufficient to saturate the test pad, then waiting a sufficient time for the protein to interact with the TBPB indicator reagent composition, and finally examining the test strip for a response, such as a color transition. TABLE II summarizes the average color space differences (ΔE) obtained at varying albumin levels for the different carrier matrices. The test strips were examined for a response approximately one minute after the test strip was removed from the test sample.

TABLE II

| COLOR SPACE DIFFERENCES FOR VARYING ALBUMIN CONCENTRATIONS USING DIFFERENT CARRIER MATRICES | | | | | |
|---|---|---|---|---|---|
| CARRIER MATRIX | ΔE (Alb5-0) | ΔE (Alb10-0) | ΔE (Alb15-0) | ΔE (Alb30-0) | ΔE (Alb100-0) |
| ALBUSTIX | 2.1 | 2.8 | 5.4 | — | 26.8 |
| POLYMERIZED URETHANE-BASED FILM (EX. 1) | 6.2 | 10.5 | 16.6 | 28.2 | 53.4 |
| POLYMERIZED URETHANE-BASED FILM (EX. 2) | 6.7 | 10.4 | 16.0 | 26.2 | 52.6 |

The data presented in TABLE II show that present day assays for protein are unable to detect or measure protein concentrations below about 15 mg/dL. For the ALBUSTIX test pad, the color space differences for solutions having 5 mg/dL and 10 mg/dL protein concentrations were 2.1 and 2.8 color blocks, respectively. Such small color space differences essentially are undetectable by to the human eye, and hence the test strip apparently would not change color. At a concentration of 15 mg/dL of protein, a marginally detectable color space difference of 5.4 color blocks occurs. Therefore, for present day test strips for protein, if no color transition occurs, then the assayer only can estimate that the sample contains less than about 15 mg/dL of protein, the color space differences are sufficiently large to detect and meausre protein, such as a ΔE of 26.8 color blocks for 100 mg/dL of protein.

However, if a carrier matrix of the present invention is included in a test device to assay for protein, an assayer can accurately and reliably determine albumin concentrations below 15 mg/dL, such as down to about 5 mg/dL. From the data summarized in TABLE II, it is seen that a detectable color space difference of greater than 6 color blocks results from contact of either of the carrier matrices manufactured from the urethane-containing compositions of Examples 1 and 2 with solutions including 5 mg/dL of albumin. Similarly, the carrier matrices of the present invention provide a more spectacular color development for samples including 10 mg/dL albumin, therefore allowing an assayer to determine whether a sample includes 5 mg/dL or 10 mg/dL of albumin. This demonstrated sensitivity to low protein concentrations is both new and unexpected in the art, and therefore allows the accurate detection and measurement of protein levels below about 15 mg/dL by a simple dry phase test strip procedure.

In addition, a more spectacular color transition also was observed at higher albumin concentrations, such as 15 mg/dL, 30 mg/dL and 100 mg/dL, when a carrier matrix of the present invention was included in the test device, thereby also providing a more sensitive, accurate and reliable protein assay at relatively high protein concentrations. For example, the color space differences for the present day ALBUSTIX test pad is only a marginally perceptible 5.4 color blocks for an albumin concentration of 15 mg/dL, whereas a test pad including a carrier matrix of the present invention produced an easily differentiable color space difference of about 16 color blocks. Therefore, the results tabulated in TABLE II show that a dry phase test strip to assay for microalbuminuria, i.e., protein concentration below about 15 mg/dL, heretofore unavailable because of technological limitations in assaying for low concentrations of protein, now is available. In addition, the carrier matrix of the present invention provides enhanced sensitivity to protein concentrations greater than about 15 mg/dL.

Accordingly, surprisingly and unexpectedly, more accurate protein assays are achieved by utilizing a carrier matrix of the present invention. In addition, the carrier matrix of the present invention further provides a method of quickly and accurately testing for proteins in a test samples by providing a carrier matrix that substantially improves assay sensitivity to allow the detection and measurement of low protein concentrations, such as about 5 mg/dL. Therefore, in general, it has been found that curing a suitable urethane-containing composition provides a carrier matrix that improves the sensitivity, accuracy and precision of dry phase test strip protein assays, especially for low protein concentrations.

In accordance with another important feature of the present invention, it also has been demonstrated that dissolving or dispersing the urethane compound in a liquid vehicle comprising from about 30% to about 70% by weight of an aprotic solvent, like dimethylformamide, and from about 30% to about 70%, and preferably from about 35% to about 60%, by weight of an alcohol, such as methyl alcohol, ethyl alcohol or isopropyl alcohol, reduces the curing time of the urethane-containing composition to as low as about 30 seconds. In addition, a solvent blend reduces the unpleasant aprotic solvent odors; and still provides for the greater response, and therefore the increased sensitivity, to protein in a liquid test sample.

It should be noted that the polymerized urethane-based compound provides a carrier matrix that gives a more spectacular color transition compared to a carrier matrix comprising a bibulous substrate, like filter paper. Overall, it has been demonstrated that color space differences are improved by using the carrier matrix of the present invention in a dry phase test strip assay for proteins. Therefore, the carrier matrix of the present invention provides an improved test pad for use in a dry phase test strip designed for the assay of proteins. Consequently, employing the carrier matrix of the present invention dramatically increases protein assay sensitivity, especially to low protein concentrations, therefore providing an improved dry phase test strip procedure to assay for proteins.

In regard to using a polymerized urethane-based film, layer or membrane as the carrier matrix for the indicator reagent composition in the assay for proteins, it has been found that a membrane, layer or film obtained by curing either the composition of Example 1 or by curing the composition of Example 2 gives excellent color differentiation and excellent color stability even after the test sample is wiped dry from the membrane. For example, for analyte test devices using membranes or films derived from curing the compositions of Example 1 or Example 2, the color transition resulting from contact with albumin showed no visual deterioration in color intensity or depth over a several day period. In accordance with an important feature of the present invention, the color generated in response to the albumin content is determined either visually or instrumentally and either with the test sample remaining in contact with the carrier matrix or after the sample is wiped from the carrier matrix. Furthermore, it should be understood that Examples 1 and 2 are only nonlimiting examples of urethane-containing compositions that can be cured to provide carrier matrices that give accurate protein determinations, especially at low protein concentrations.

Therefore, in accordance with an important feature of the present invention, more accurate and reliable assays for the total protein content in urine and other liquid test samples can be performed by utilizing the carrier matrix of the present invention in a dry phase test strip assay for proteins. The carrier matrix of the present invention improves the color resolution of the assay, and therefore improves assay sensitivity, especially at low albumin levels of approximately 30 mg/dL and below. Furthermore, by performing the assay with a dry phase test strip that includes the carrier matrix of the present invention, a new and unexpectedly accurate method of determining the presence or concentration of low amounts of protein, such as about 5 mg/dL, in the test sample is provided.

Obviously, many modifications and variations of the invention as hereinbefore set forth can be made without departing from the spirit and scope thereof and therefore only such limitations should be imposed as are indicated by the appended claims.

What is claimed and sought to be secured by Letters Patent of the United States is:

1. A method of manufacturing a test pad for determining the presence or concentration of a predetermined chemical compound in a test fluid comprising:

forming a layer of a urethane-containing composition, the urethane-containing composition comprising from about 0.1% to about 10% by weight of a urethane compound, from about 1% to about 10% by weight of a water-insoluble inorganic compound, and from about 10% to about 40% by weight of an insoluble organic compound, based on the total weight of the urethane-containing composition, dispersed in a suitable liquid vehicle;

curing the layer of the urethane-containing composition to remove a substantial portion the liquid vehicle and to form a carrier matrix;

drying the carrier matrix, incorporating an indicator reagent composition, capable of a detectable interaction with the predetermined chemical compound, into the carrier matrix to form a test pad; and drying the test pad.

2. The method of claim 1 wherein the urethane compound in the urethane-containing composition is a polymerizable urethane compound, a polymerized urethane compound, or a combination thereof.

3. The method of claim 2 wherein the urethane compound is a polymerizable urethane compound selected from the group consisting of a urethane prepolymer, urethane oligomer, and incompletely-cured urethane polymer and combinations thereof.

4. The method of claim 2 wherein the urethane compound is a polymerizable urethane compound having a weight average molecular weight in the range of from about 30,000 to about 500,000.

5. The method of claim 1 wherein the urethane compound is present in the urethane-containing composition in an amount ranging from about 1% to about 5% by weight based on the total weight of the urethane-containing composition.

6. The method of claim 1 wherein the water-insoluble inorganic compound in the urethane-containing composition is selected from the group consisting of calcium sulfate, titanium dioxide, alumina, zinc oxide, magnesium oxide, calcium oxide, silicon dioxide, talc, magnesium titanium oxide, barium oxide, barium sulfate, strontium sulfate and combinations thereof.

7. The method of claim 1 wherein the water-insoluble inorganic compound is present in the urethane-containing composition in an amount ranging from about 2% to about 5% by weight based on the total weight of the urethane-containing composition.

8. The method of claim 1 wherein the insoluble organic compound in the urethane-containing composition is a microcrystalline cellulose, a microcrystalline nitrocellulose or a combination thereof.

9. The method of claim 1 wherein the insoluble organic compound is present in the urethane-containing composition in an amount ranging from about 20% to about 35% by weight based on the total weight of the urethane-containing composition.

10. The method of claim 1 wherein the liquid vehicle is selected from the group consisting of an aprotic solvent, an alcohol including from one carbon atom to about four carbon atoms and combinations thereof.

11. The method of claim 10 wherein the liquid vehicle is an aprotic solvent selected from the group consisting of dimethylformamide, dimethylsulfoxide, N-methylpyrrolidone and combinations thereof.

12. The method of claim 11 wherein the aprotic solvent is dimethylformamide.

13. The method of claim 10 wherein the liquid vehicle is an alcohol selected from the group consisting of methyl alcohol, ethyl alcohol, n-propyl alcohol, isopropyl alcohol, n-butyl alcohol, sec-butyl alcohol, isobutyl alcohol, tetra-butyl alcohol and combinations thereof.

14. The method of claim 1 wherein the liquid vehicle of the urethane-containing composition is present in the urethane-containing composition in an amount ranging from about 40% to about 88.9% by weight based on the total weight of the urethane-containing composition.

15. The method of claim 1 wherein the layer of the urethane-containing composition is cured for a time ranging from about 30 seconds to about 20 minutes by heating the layer of the urethane-containing composition at a temperature in the range of about 30° C. to about 90° C.

16. The method of claim 15 wherein the layer of the urethane-containing composition is cured for a time ranging from about 30 seconds to about 2 minutes.

17. The method of claim 15 wherein the layer of the urethane-containing composition is cured in a water bath.

18. The method of claim 1 wherein the layer of the urethane-containing composition is cured for a time ranging from about 30 seconds to about 30 minutes in a sonicator bath containing water.

19. The method of claim 1 wherein the urethane-containing composition further comprises from 0% to about 5% by weight, based on the total weight of the urethane-containing composition, of a surfactant; from 0% to about 2% by weight, based on the total weight of the urethane-containing composition, of a silicon-containing material; and from 0% to about 6% by weight, based on the total weight of the urethane-containing composition, of a water-soluble cellulose derivative or a water-disperible gum.

20. The method of claim 1 wherein the predetermined chemical compound is a protein.

21. The method of claim 20 wherein the protein is albumin.

22. An analyte detection device to determine the presence or concentration of a protein in a liquid test sample comprising a carrier matrix incorporating therein an indicator reagent composition capable of interacting with the protein to produce a detectable or measurable response in the carrier matrix, wherein the carrier matrix is permeable to the liquid test sample and comprises a polymerized layer of a urethane-based compound, wherein the polymerized layer of the urethane-based compound is formed from a urethane-containing composition including from about 0.1% to about 10% by weight of a urethane compound, from about 1% to about 10% by weight of a water-insoluble inorganic compound, from about 10% to about 40% by weight of an insoluble organic compound, and from about 40% to about 88.9% by weight of a suitable liquid vehicle, based on the total weight of the urethane-containing composition.

23. The analyte detection device of claim 22 wherein the polymerized layer of the urethane-based compound is formed from a urethane-containing compound composition including from about 1% to about 5% by weight of the urethane compound.

24. The analyte detection device of claim 22 wherein the water-insoluble inorganic compound in the urethane-containing composition is selected from the group consisting of calcium sulfate, titanium dioxide, alumina, zinc oxide, magnesium oxide, calcium oxide, silicon dioxide, talc, magnesium aluminum oxide, magnesium titanium oxide, barium oxide, barium sulfate, strontium sulfate and combinations thereof.

25. The analyte detection device of claim 22 wherein the water-insoluble inorganic compound is present in the urethane-containing composition in an amount ranging from about 2% to about 5% by weight of the urethane-containing composition.

26. The analyte detection device of claim 22 wherein the insoluble organic compound in the urethane-containing composition is a microcrystalline cellulose, a microcrystalline nitrocellulose or a combination thereof.

27. The analyte detection device of claim 22 wherein the insoluble organic compound is present in the urethane-containing composition in an amount ranging from about 20% to about 35% by weight based on the total weight of the urethane-containing composition.

28. A method of determining the presence or concentration of a protein in a test fluid comprising:
  (a) contacting the test fluid with an analyte detection device comprising a test pad including a carrier matrix and an indicator reagent composition, wherein the indicator reagent composition is capable of exhibiting a detectable response upon interaction with the protein, and wherein the carrier matrix comprises a polymerized layer of a urethane-based compound, wherein the polymerized layer of the urethane-based compound is formed from a urethane-containing composition including from about 0.1% to about 10% by weight of a urethane compound, from about 1% to about 10% by weight of a water-insoluble inorganic compound, from about 10% to about 40% by weight of an insoluble organic compound and from about 40% to about 88.9% by weight of a suitable liquid vehicle, based on the total weight of the urethane-containing composition; and
  (b) examining the analyte detection device for a response to the protein content of the test fluid.

29. The method of claim 23 wherein the detectable response is a color transition.

30. The method of claim 28 wherein the test fluid comprises a biological test fluid.

31. The method of claim 28 wherein the protein is albumin.

32. The method of claim 31 wherein the test fluid includes about 10 mg/dL or less of albumin.

33. A method of manufacturing a carrier matrix for use in a test device to determine the presence or concentration of a predetermined chemical compound present in a test fluid in amounts as low as about 5 mg/dL comprising:
  forming a layer of a urethane-containing composition comprising a urethane compound, a water-insoluble inorganic compound and an insoluble organic compound dispersed in a suitable liquid vehicle;
  curing the layer of the urethane-containing composition to remove a substantial portion of the liquid vehicle and to form the carrier matrix; and
  drying the carrier matrix.

34. The method of claim 33 wherein after drying the carrier matrix, an indicator reagent composition capable of undergoing a detectable or measurable response upon interaction with the predetermined chemical compound in the test fluid is incorporated into the carrier matrix.

35. The method of claim 33 wherein an indicator reagent composition capable of undergoing a detectable or measurable response upon interaction with the predetermined chemical compound in the test fluid is incorporated into the urethane-containing composition prior to curing the layer of the urethane-containing composition.

36. A carrier matrix permeable to a fluid test sample for use in an analyte detection device to determine the presence or concentration of a predetermined analyte in the fluid test sample comprising a polymerized layer of a urethane-based compound, wherein the polymerized layer of the urethane-based compound is formed from a composition including from about 0.1% to about 10% by weight of a urethane compound, from about 1% to about 10% by weight of a water-insoluble inorganic compound, from about 10% to about 40% by weight of an insoluble organic compound and from about 40% to about 88.9% by weight of a suitable liquid vehicle, based on the total weight of the urethane-containing composition.

* * * * *